US011471668B2

(12) United States Patent
Salvatierra et al.

(10) Patent No.: US 11,471,668 B2
(45) Date of Patent: Oct. 18, 2022

(54) APPARATUS AND METHODS FOR MAKING COCHLEAR IMPLANT ELECTRODE ARRAYS

(71) Applicant: ADVANCED BIONICS AG, Staefa (CH)

(72) Inventors: Candelaria Salvatierra, West Lancaster, CA (US); Bing Xu, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 201 days.

(21) Appl. No.: 16/724,291

(22) Filed: Dec. 21, 2019

(65) Prior Publication Data

US 2021/0187282 A1 Jun. 24, 2021

(51) Int. Cl.
*A61N 1/36* (2006.01)
*A61N 1/05* (2006.01)
*A61F 11/20* (2022.01)

(52) U.S. Cl.
CPC ....... *A61N 1/0541* (2013.01); *A61N 1/36038* (2017.08); *A61F 11/20* (2022.01)

(58) Field of Classification Search
CPC .. A61N 1/0541; A61N 1/36038; A61F 11/004
See application file for complete search history.

(56) References Cited

U.S. PATENT DOCUMENTS

| 4,686,765 A | 8/1987 | Byers et al. |
| 5,000,194 A | 3/1991 | Van Den Honert et al. |
| 5,037,497 A | 8/1991 | Stypulkowski |
| 5,123,422 A | 6/1992 | Charvin |
| 5,439,485 A | 8/1995 | Mar et al. |
| 5,534,022 A | 7/1996 | Hoffmann et al. |
| 5,542,173 A | 8/1996 | Mar et al. |
| 5,580,699 A | 12/1996 | Layman et al. |
| 5,658,709 A | 8/1997 | Layman et al. |
| 5,824,022 A | 10/1998 | Zilberman et al. |
| 6,125,302 A | 9/2000 | Kuzma |

(Continued)

FOREIGN PATENT DOCUMENTS

| WO | WO2018/031025 A1 | 2/2018 | |
| WO | WO-2018031025 A1 * | 2/2018 | ........... A61N 1/0541 |

(Continued)

OTHER PUBLICATIONS

U.S. Appl. No. 16/319,638, filed Jan. 22, 2019, U.S. Pat. No. 11,103,703 B2.

(Continued)

*Primary Examiner* — Ankit D Tejani
*Assistant Examiner* — Joshua Brendon Solomon
(74) *Attorney, Agent, or Firm* — Henricks Slavin LLP (57) ABSTRACT

A method that may include the steps of positioning a contact assembly, including a plurality of electrically conductive contacts that are respectively connected to a plurality of lead wires, on a shell formed from a first resilient material to form an electrode array sub-assembly, positioning the electrode array subassembly in a cochlear implant electrode array mold, and introducing a second resilient material into the mold to form a cochlear implant electrode array flexible body, on which the contacts are located, that is defined by the first and second flexible materials.

17 Claims, 9 Drawing Sheets

(56) References Cited

U.S. PATENT DOCUMENTS

| | | |
|---|---|---|
| 6,144,883 A | 11/2000 | Kuzma |
| 6,195,586 B1 | 2/2001 | Kuzma |
| 6,309,410 B1 | 10/2001 | Kuzma et al. |
| 6,374,143 B1 | 4/2002 | Berrang et al. |
| 6,421,569 B1 | 7/2002 | Treaba et al. |
| 7,451,000 B2 | 11/2008 | Gibson et al. |
| 8,461,042 B2 | 6/2013 | Dadd et al. |
| 8,620,459 B2 | 12/2013 | Gibson et al. |
| 8,782,884 B2 | 7/2014 | Capcelea et al. |
| 9,694,174 B2 | 7/2017 | Dadd et al. |
| 10,406,350 B2 | 9/2019 | Mercanzini et al. |
| 11,103,703 B2 | 8/2021 | Krywcun et al. |
| 2003/0171787 A1 | 9/2003 | Money et al. |
| 2009/0306745 A1 | 12/2009 | Parker et al. |
| 2010/0036470 A1 | 2/2010 | Nielsen |
| 2010/0287770 A1 | 11/2010 | Dadd et al. |
| 2011/0016710 A1 | 1/2011 | Dadd et al. |
| 2011/0126410 A1 | 6/2011 | Capcelea et al. |
| 2013/0079749 A1 | 3/2013 | Overstreet et al. |
| 2013/0238074 A1 | 9/2013 | Zimmerling |
| 2014/0163662 A1 | 6/2014 | Beerling et al. |
| 2015/0032194 A1 | 1/2015 | Mergen et al. |
| 2015/0148736 A1 | 5/2015 | Jolly et al. |
| 2015/0246234 A1 | 9/2015 | Hazard et al. |
| 2016/0022990 A1 | 1/2016 | Risi |
| 2016/0082249 A1 | 3/2016 | Thenuwara et al. |
| 2016/0193460 A1 | 7/2016 | Xu et al. |
| 2017/0056646 A1* | 3/2017 | Sibary .................. A61N 1/0541 |
| 2020/0188666 A1 | 6/2020 | Krywcun et al. |
| 2020/0384262 A1* | 12/2020 | Hoffman .............. A61N 1/0541 |
| 2021/0106816 A1 | 4/2021 | Clabeaux et al. |
| 2021/0236808 A1 | 8/2021 | Wise et al. |
| 2021/0346697 A1 | 11/2021 | Krywcun et al. |

FOREIGN PATENT DOCUMENTS

| | | | |
|---|---|---|---|
| WO | WO2018/209872 A1 | 11/2018 | |
| WO | WO-2018102695 A8 * | 11/2018 | ........... A61N 1/0541 |

OTHER PUBLICATIONS

U.S. Appl. No. 17/384,666, filed Jul. 23, 2021, 2021/0346697 A1.
U.S. Appl. No. 16/599,102, filed Oct. 10, 2019, 2021/0106816 A1.
U.S. Appl. No. 16/724,291, filed Dec. 21, 2019, 2021/0187282 A1.
U.S. Appl. No. 17/232,131, filed Apr. 15, 2021, 2021/0236808 A1.
U.S. Appl. No. 16/319,638, filed Jan. 22, 2019, 2020/0188666 A1.
U.S. Appl. No. 16/724,291, filed Dec. 21, 2019.
U.S. Appl. No. 17/232,131, filed Apr. 15, 2021.

* cited by examiner

APPARATUS AND METHODS FOR MAKING COCHLEAR IMPLANT ELECTRODE ARRAYS

BACKGROUND

1. Field

The present disclosure relates generally to the implantable portion of implantable cochlear stimulation (or "ICS") systems and, in particular, to electrode arrays.

2. Description of the Related Art

Figure 1:
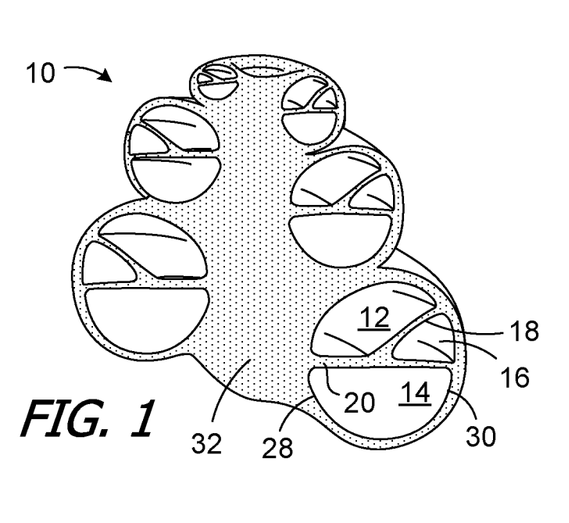
FIG. 1 is a section view of a cochlea.
Figure 2:
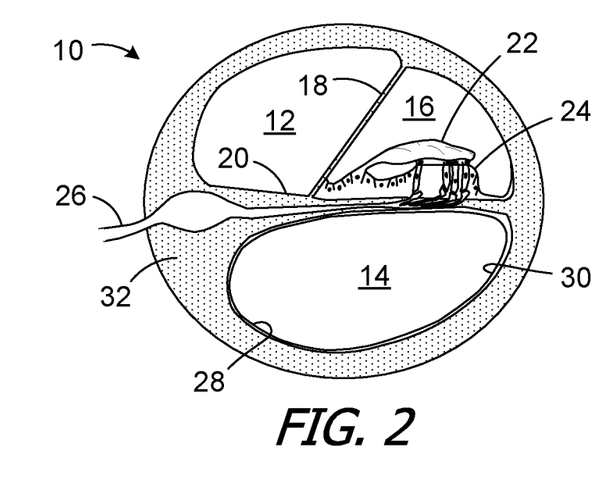
FIG. 2 is another section view of the cochlea.

Referring to FIGS. 1 and 2, the cochlea 10 of the inner ear is a hollow, helically coiled, tubular bone (similar to a nautilus shell) that is divided into the scala vestibuli 12, the scala tympani 14 and the scala media 16 by the Reissner's membrane 18 and the basilar membrane 20. The cochlea 10, which typically includes approximately two and a half helical turns, is filled with a fluid that moves in response to the vibrations coming from the middle ear. As the fluid moves, a tectorial membrane 22 and thousands of hair cells 24 are set in motion. The hair cells 24 convert that motion to electrical signals that are communicated via neurotransmitters to the auditory nerve 26, and transformed into electrical impulses known as action potentials, which are propagated to structures in the brainstem for further processing. Many profoundly deaf people have sensorineural hearing loss that can arise from the absence or the destruction of the hair cells 24 in the cochlea 10. Other aspects of the cochlea 10 illustrated in FIGS. 1 and 2 include the medial wall 28, the lateral wall 30 and the modiolus 32.

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a sound processor, converted to a pulse sequence having varying pulse widths, rates, and/or amplitudes, and transmitted to an implanted receiver circuit of the ICS system. The implanted receiver circuit is connected to an implantable lead with an electrode array that is inserted into the cochlea, and electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

As alluded to above, some ICS systems include an implantable cochlear stimulator (or "cochlear implant") having a lead with an electrode array, a sound processor unit (e.g., a body worn processor or behind-the-ear processor) that communicates with the cochlear implant, and a microphone that is part of, or is in communication with, the sound processor unit. The cochlear implant electrode array, which is formed by a molding process, includes a flexible body formed from a resilient material and a plurality of electrically conductive contacts (e.g., sixteen platinum contacts) spaced along a surface of the flexible body. The contacts of the array are connected to lead wires that extend through the flexible body. Exemplary cochlear leads are illustrated in U.S. Pat. Nos. 5,037,497 and 8,620,459 and US Pat. Pub. No. 2010/0287770.

The present inventors have determined that conventional cochlear implant electrode arrays, as well as conventional methods of making such arrays, are susceptible to improvement. For example, many electrode arrays have a preset spiral or otherwise curved shape that leads to challenges during the molding processes. The present inventors have determined that it can be difficult to handle the electrode array components and to properly position the components within the mold. The present inventors have determined that the lead wires connected to the electrode array contacts may be detached or broken when the electrode array is straightened (e.g., with a stylet) for the insertion process.

SUMMARY

A method of forming an electrode array in accordance with one of the present inventions includes the steps of positioning a contact assembly, including a plurality of electrically conductive contacts that are respectively connected to a plurality of lead wires, on a shell formed from a first resilient material to form an electrode array sub-assembly, positioning the electrode array subassembly in a cochlear implant electrode array mold, and introducing a second resilient material into the mold to form a cochlear implant electrode array flexible body, on which the contacts are located, that is defined by the first and second flexible materials.

There are a number of advantages associated with such methods. By way of example, but not limitation, the present methods make it easier to handle the electrode array components and to properly position the components within a mold. In some instances, the shell may be provided with strain relief elements that reduce the likelihood that the lead wires of a completed electrode array contacts will be broken or detached when the electrode array is straightened.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

The present apparatus and methods may be used to manufacture a wide variety of cochlear leads, and such cochlear leads may form part of a cochlear implant (or "implantable cochlear stimulator"). One example of such a cochlear implant is generally represented by reference numeral 100 in FIG. 3 and includes an exemplary stimulation assembly 102 and an exemplary cochlear lead 104.

Figures 3, 4, 5:
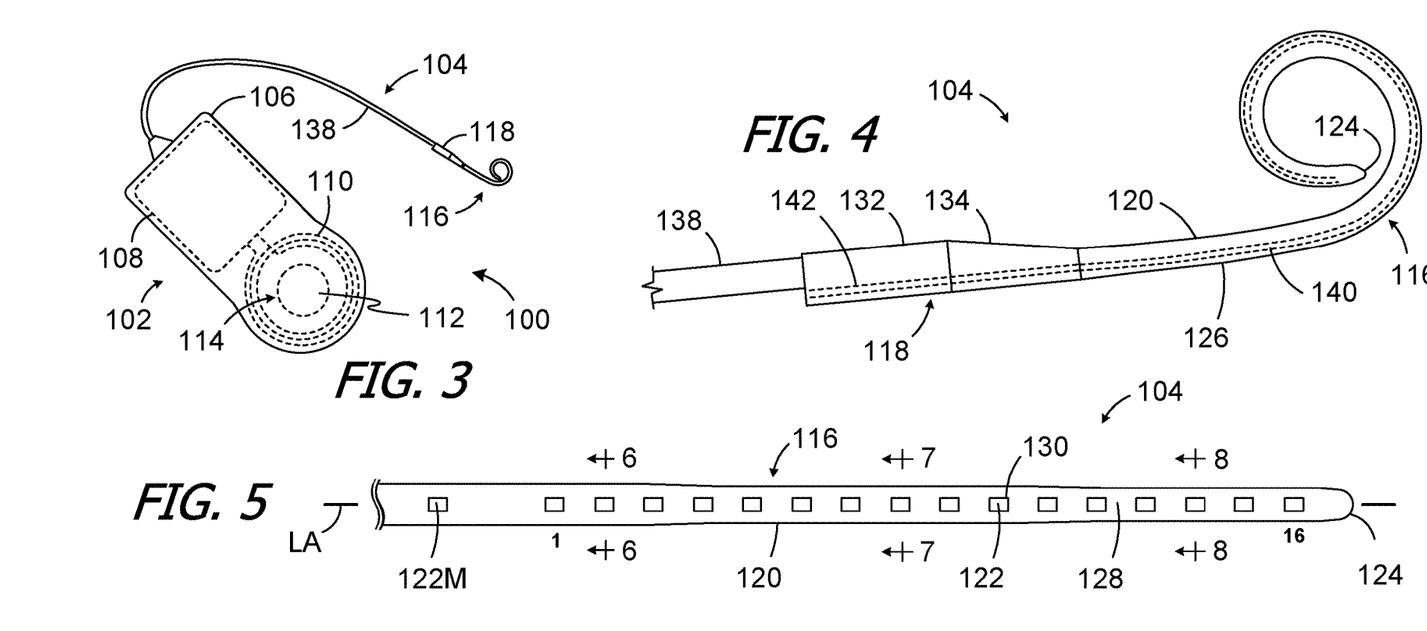
FIG. 3 is a top view of a cochlear implant in accordance with one embodiment of a present invention.
FIG. 4 is a side view of a cochlear lead electrode array in accordance with one embodiment of a present invention.
FIG. 5 is a bottom view of the cochlear lead electrode array illustrated in FIG. 4 in a straightened state.

The exemplary stimulation assembly 102 includes a flexible housing 106 formed from a silicone elastomer or other suitable material, a processor assembly 108, an antenna 110 that may be used to receive data and power by way of an external antenna that is associated with, for example, a sound processor unit, and a positioning magnet 112 located within a magnet pocket 114. The magnet 112 is used to maintain the position of a sound processor unit (or sound processor unit headpiece) over the antenna 110. The cochlear implant may, in some instances, be configured is manner that facilitates magnet removal and replacement. Here, the housing 106 may be provided with a magnet aperture (not shown) that extends from the magnet pocket 114 to the exterior of the housing.

Referring to FIGS. 4-8, the exemplary cochlear lead 104 includes an electrode array 116 and, in at least some instances, a wing 118 that functions as a handle for the surgeon during the implantation surgery. The exemplary electrode array 116 has a flexible body 120 and a plurality of electrically conductive contacts 122 (e.g., the sixteen contacts 122 illustrated in FIG. 4) spaced along the flexible body between the tip (or "apical") end 124 and the base (or "basal") end 126. The electrically conductive contacts 122 (or "contacts") may be located inward of the flexibly body outer surface 128 and exposed by way of a corresponding plurality of contact windows (or "windows") 130 that extend through the outer surface to the contacts. The width of the windows 130 is not limited to the widths illustrated in FIGS. 6-8 and, in other implementations, the width of the windows 130 may be less than the illustrated width, greater than the illustrated width, or equal to the width of the contacts 122, as may be determined based on system requirements. The length of the windows 130 (visible in FIG. 5) is not limited to the illustrated length, and may be greater than or less than the illustrated length in other implementations based on system requirements. The wing 118 may include a rectangular portion 132 and a tapered portion 134. The contacts 122 are each connected to a respective lead wire 136, and the lead wires together define a wire bundle 137 (FIG. 6) that extends through the flexible body 120. In addition to functioning as a handle, the wing 118 provides tension relief for lead wires 136 (FIGS. 6-8) that do not run straight through the wing. A tubular member 138, which may consist of tubes of different sizes, extends from the wing 118 to the housing 106. The lead wires 136 extend through the tubular member 138. The connection between the stimulation assembly 102 and a cochlear lead 104 may be a temporary connection, whereby the stimulation assembly and a cochlear lead may be disconnected from one another (e.g., for in situ replacement of the stimulation assembly), or a permanent connection.

The exemplary electrode array 116 also has preset spiral shape (e.g. a helical shape) with a tight curvature (resulting from the mold shape) in an unstressed state that corresponds to the interior geometry of the cochlea. The spiral electrode array 116 may be straightened prior to the insertion process by a stylet or other stiffening element that is inserted into a stylet lumen 140 within the electrode array. During use, the apical ends of electrode array 116 and stylet may be inserted into the basal region of the cochlea by way of the round window or a cochleostomy and, as the electrode array moves deeper into the cochlea, the electrode array is advanced off the stylet. The portions of the electrode array 116 advanced off the stylet return their relaxed, curved shape. This process continues until the electrode array 116 reaches the desired position within the cochlea. The remainder of the stylet is then withdrawn from the stylet lumen 140, leaving the cochlear lead 104 in place.

Although the present inventions are not so limited, the flexible body 120 of the exemplary electrode array 116 has a non-circular shape with a flat bottom (note FIGS. 6-8) in a cross-section perpendicular to the longitudinal axis LA. The flexible body 120 may also be tapered, with a perimeter in a plane perpendicular to the longitudinal axis LA that is smaller at the tip end 124 than at the base end 126. The shape of the flexible body 120 may also vary along the length of the flexible body. Any other suitable flexible body shape (e.g., circular or oval), with or without a flat surface, may also be employed. Suitable materials for the flexible body 120 include, but are not limited to, electrically non-conductive resilient materials such as LSR, high temperature vulcanization ("HTV") silicone rubbers, room temperature vulcanization ("RTV") silicone rubbers, and thermoplastic elastomers ("TPEs").

Figure 6:
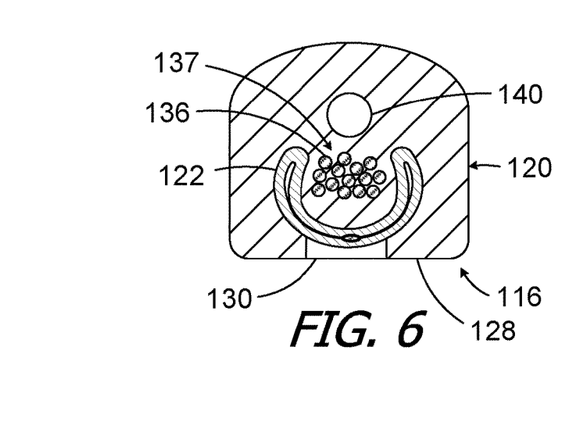
FIG. 6 is a section view taken along line 6-6 in FIG. 5.
Figure 7:
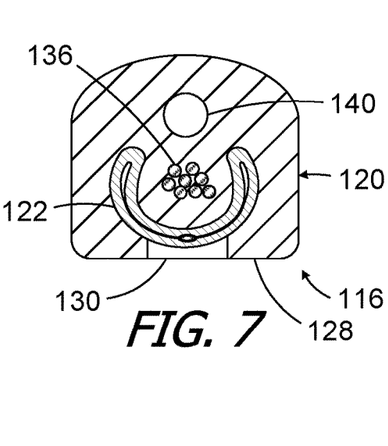
FIG. 7 is a section view taken along line 7-7 in FIG. 5.
Figure 8:
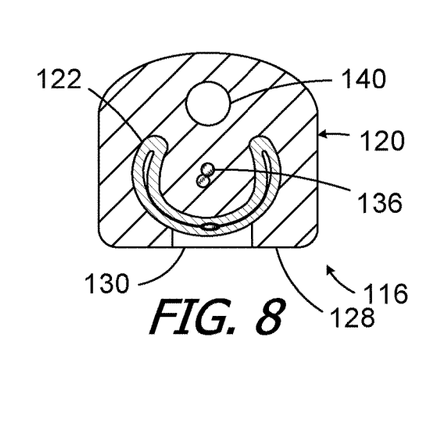
FIG. 8 is a section view taken along line 8-8 in FIG. 5.
Figure 9:
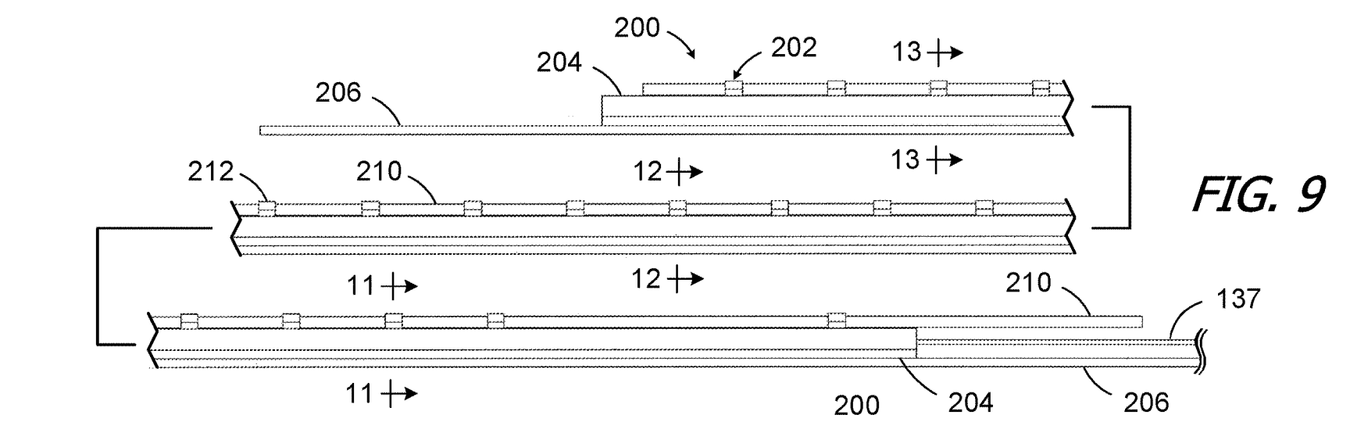
FIG. 9 is a side view of a cochlear lead electrode array sub-assembly in accordance with one embodiment of a present invention.
Figure 10:
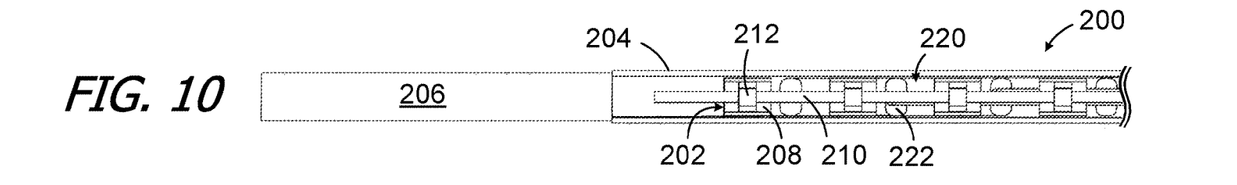
FIG. 10 is a top view of a portion the cochlear lead electrode array sub-assembly illustrated in FIG. 9.

As illustrated for example in FIG. 5, the exemplary contacts 122 may be referred to in numbered order, 1st through 16th in the sixteen contact illustrated implementation, with the contact closest to the tip end 124 being the 1st contact and the contact closest to the base end 126 being the 16th contact. An additional contact 122M, which is not connected to a lead wire 136, may also be provided. Suitable materials for the contacts 122 include, but are not limited to, platinum and platinum-iridium. The exemplary contacts 122 may be have a partial circle shape as is shown in FIGS. 6-8 and, as is discussed in greater detail below with reference to FIGS. 16-21, may be formed by a placing a tubular workpiece into an appropriately shaped fixture, placing the end of a lead wire into the workpiece, and then applying heat and pressure to the workpiece to compress the workpiece onto the lead wire. The contacts 122 may be the same size (as shown) or different sizes (e.g., larger at the apical end), and/or may be the same shape (as shown) or different shapes. Various examples of tubular workpieces being compressed onto lead wires are described in WO2018/031025A1 and WO2018/102695A1, which are incorporated herein by reference.

Figure 11:
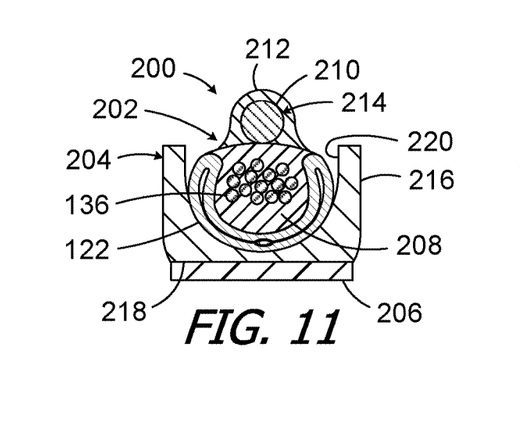
FIG. 11 is a section view taken along line 11-11 in FIG. 9.
Figure 12:
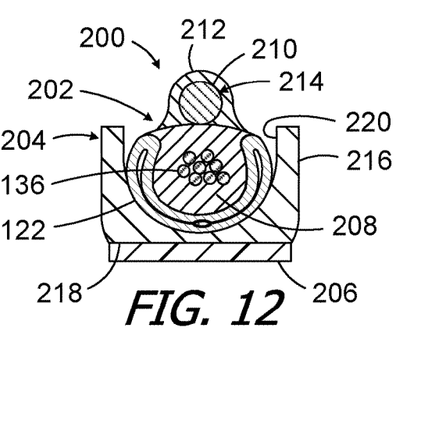
FIG. 12 is a section view taken along line 12-12 in FIG. 9.
Figure 13:
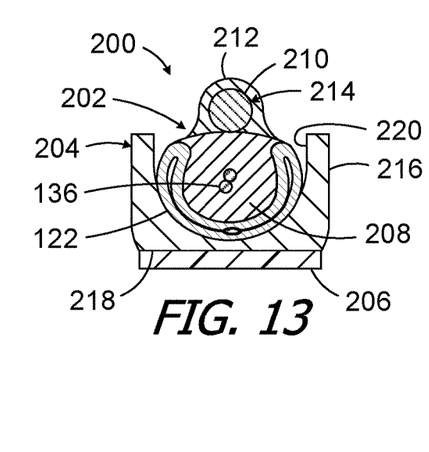
FIG. 13 is a section view taken along line 13-13 in FIG. 9.

One example of an electrode array sub-assembly (or "sub-assembly") that may be used to form an electrode array (e.g., the electrode array 116) is generally represented by reference numeral 200 in FIGS. 9-15. The exemplary sub-assembly 200 includes a contact assembly 202 and a shell 204 and, in the illustrated implementation, the sub-assembly 200 is mounted on a malleable strip 206. The sub-assembly 200 will be incorporated into the associated electrode array, while the malleable strip 206 will be removed after the molding process is complete, as is discussed below. In addition to the aforementioned contacts 122 and lead wires 136, the exemplary contact assembly 202 includes a plurality of wire carriers 208, a removable lumen formation rod 210 and a plurality of rod holders 212. The wire carriers 208 each hold the portion of the lead wires 136 that pass through that particular wire carrier at locations in spaced relation to the inner surfaces of the contacts 122. The rod holders 212 each have an aperture 214 through which the lumen formation rod 210 passes. The apertures 214 form part of the stylet lumen 140 when the rod 210 is removed after the molding process as, is discussed below. The exemplary shell 204 includes side and bottom walls 216 and 218 that define a channel 220, and the contact assembly 202 is located within the channel 220. The size and shape of the channel 220 in planes perpendicular to the longitudinal axis is similar to those of the contacts 122, as can be seen in FIGS. 11-13, and the contacts may be held in place with a small quantity of the material used to form the shell or some other suitable adhesive. A plurality of strain relief protrusions 222 that define cavities 224 therebetween are also located within the channel 220 in the illustrated implementation.

Figure 14:
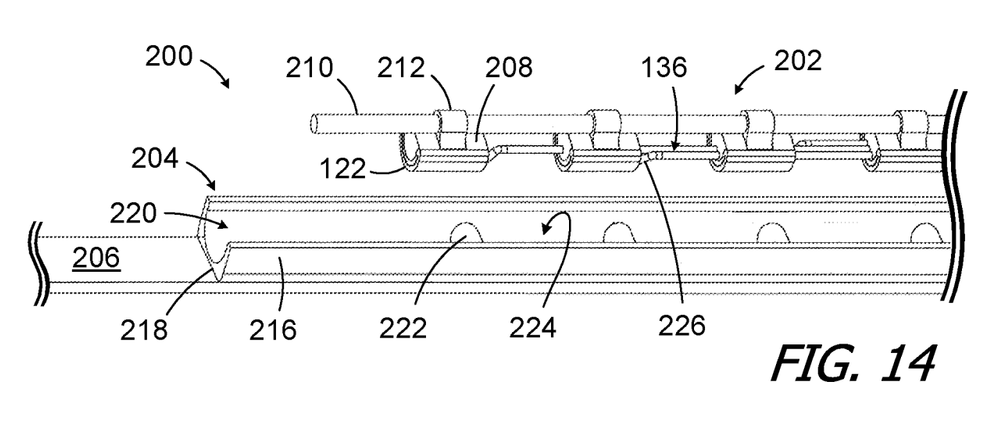
FIG. 14 is an exploded view of a portion the cochlear lead electrode array sub-assembly illustrated in FIG. 9.
Figure 15:
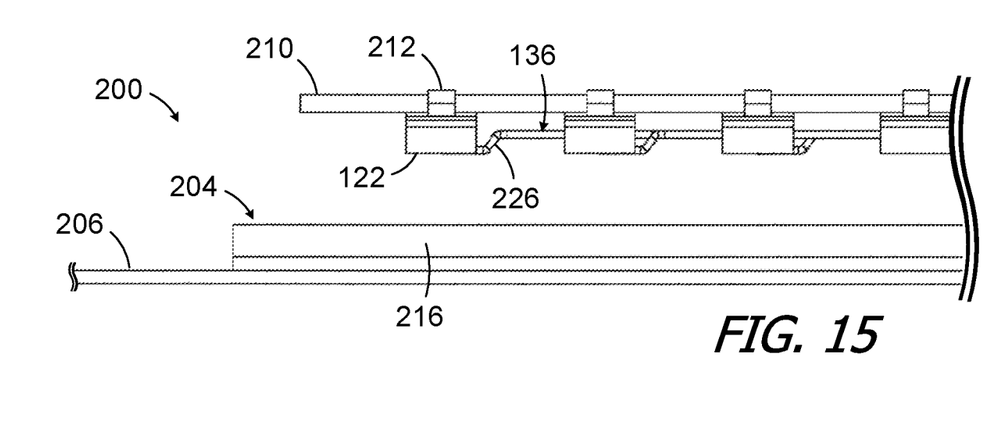
FIG. 15 is an exploded view of a portion the cochlear lead electrode array sub-assembly illustrated in FIG. 9.
Figure 16:
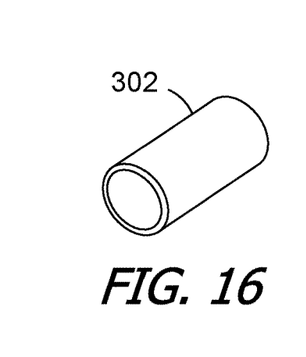
FIG. 16 is a perspective view of a contact workpiece that may be employed in a method in accordance with one embodiment of a present invention.

Referring more specifically to FIGS. 14 and 15, each contact 122 is positioned adjacent to a respective one of the strain relief protrusions 222 when the contacts are inserted into the channel 220. Each strain relief protrusion 222 deflects a portion 226 of the lead wire 136 associated with the adjacent contact 122 as the contacts are inserted into the channel 220. The lead wires 136 slide slightly relative to the wire carriers 208 as the lead wire portion 226 is deflected. The deflected portion 226 increases the between-the-contacts length of the lead wires 136, thereby creating slack in the lead wires 136 that prevents the lead wires from being broken or detached when the electrode array 116 is straightened.

With respect to materials, the contact assembly wire carriers 208 and rod holders 212 and/or the shell 204 may be formed from the same material as the cochlear lead flexible body 120 which, as noted above, includes but is not limited to LSR, HTV silicone rubbers, RTV silicone rubbers, and TPEs. As a result, the wire carrier material, rod holder material and shell material will combine with the flexible body material to form a one piece, unitary structure formed from a single common material. In other instances, the shell 204 may be formed from a material that is different than the remainder of the flexible body 120 in order to provide an electrode array with particular properties that are necessary or desired. For example, the shell 204 may be formed from material that is more flexible, or is less flexible, than the material used to form the remainder of the flexible body 120. Alternatively, or in addition, the shell 204 may be formed from drug eluting material. The shell 204 may also be a molded or printed object. The malleable strip 206 may be formed from any suitable metal or polymer. A thin layer of silicone adhesive (e.g., less than 10 μm of MED 4213 adhesive from NuSil™) may be used to secure the shell 204 to the malleable strip 206. The lumen formation rod 210 may be formed from materials such as fluoro-polymers or other polymeric monofilaments that do not bond to liquid silicone rubber (e.g., PTFE). It should also be noted that the lead wires 136 have electrical insulation that does not bond well with the LSR or other material that forms wire carriers 208. Although the bond is strong enough to maintain the spacing between the contacts 122 when the contact assembly 202 is being handled. The relatively weak bond facilitates sliding of the lead wires relative to the wire carriers when the lead wires are engaged by the strain relief protrusions 222. Sliding may be further facilitated by applying isopropyl alcohol ("IPA") to the lead wires 136 while the entire contact assembly 202 is inserted into the mold (see FIG. 30).

One exemplary method of forming contact assemblies, such as the exemplary contact assembly 202 with contacts 122, is illustrated in FIGS. 16-24. Referring first to FIGS. 16-21, the method may involve the use of an exemplary fixture 300 and workpieces 302. The fixture 300 includes a plate 304 with a surface 306 that defines an elongate semi-circular cavity 308. The top surface 306 also includes markers 310 that correspond to the intended locations of the contacts 122. Here, there is a single marker 310 for each of the contacts 122. Markers 310a and 310b respectively mark the apical end and basal end contact locations. In another implementation (not shown), a set of four markers 310 (two on each side of the cavity 308) may be provided for each of the contacts 122. Although not limited to any particular shape, the exemplary workpiece 302 is a cylindrical tube and is circular in cross-section.

Figure 17:
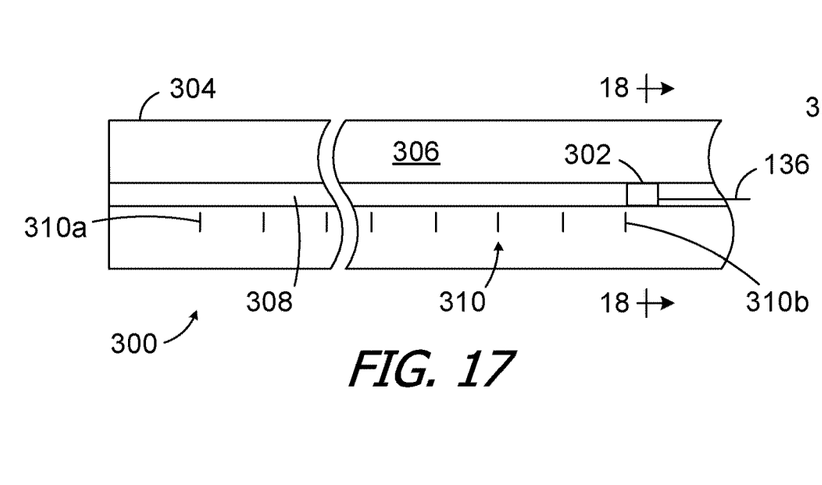
FIG. 17 is a top view of a portion of a method in accordance with one embodiment of a present invention.
Figure 18:
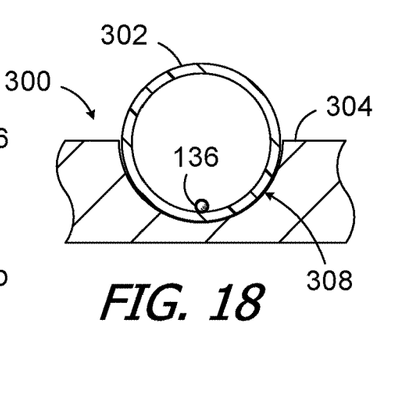
FIG. 18 is a section view taken along line 18-18 in FIG. 17.
Figure 19:
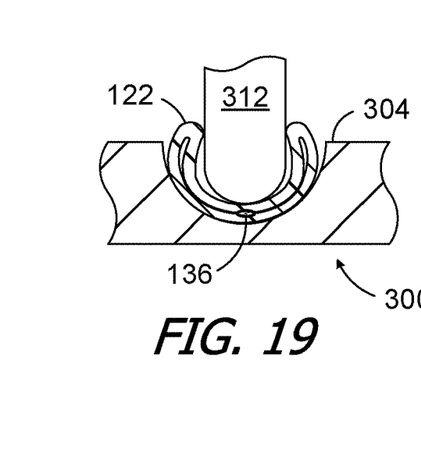
FIG. 19 is a partial section view of a portion of a method in accordance with one embodiment of a present invention.
Figure 20:
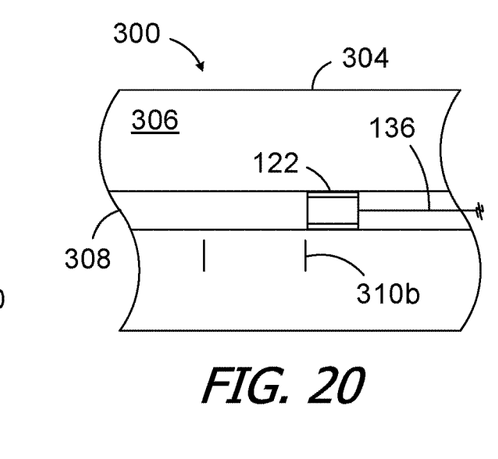
FIG. 20 is a top view of a portion of a method in accordance with one embodiment of a present invention.
Figure 21:
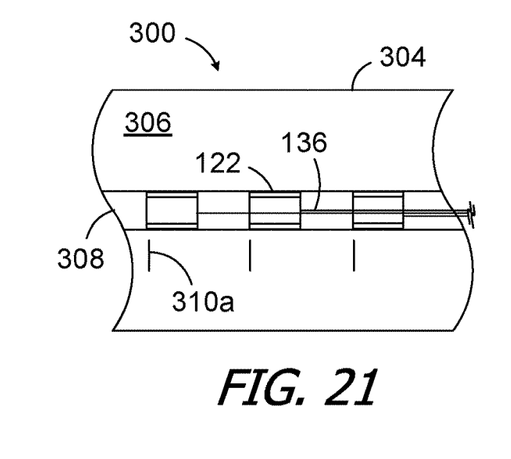
FIG. 21 is a top view of a portion of a method in accordance with one embodiment of a present invention.
Figure 22:
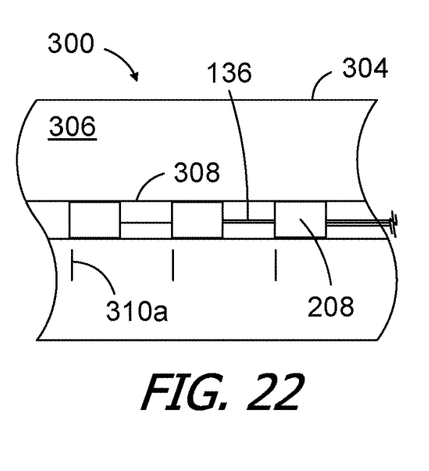
FIG. 22 is a top view of a portion of a method in accordance with one embodiment of a present invention.
Figure 23:
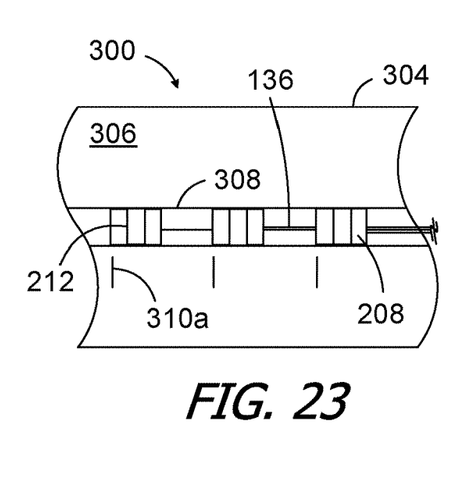
FIG. 23 is a top view of a portion of a method in accordance with one embodiment of a present invention.
Figure 24:
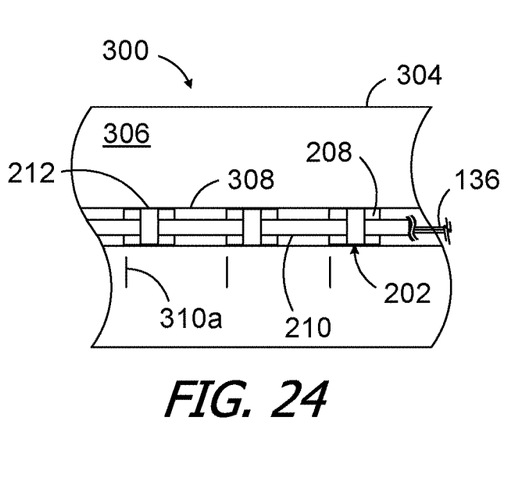
FIG. 24 is a top view of a portion of a method in accordance with one embodiment of a present invention.
Figure 25:
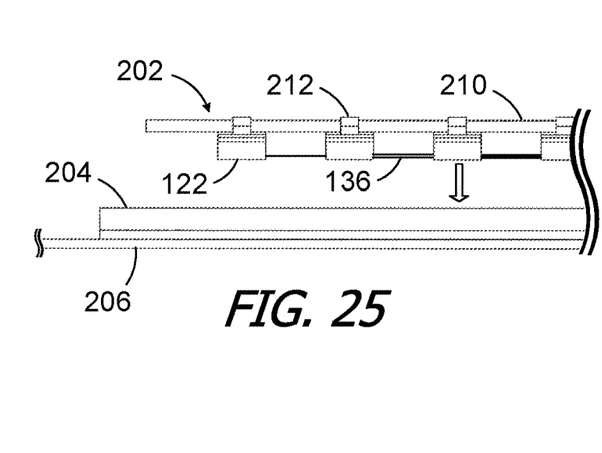
FIG. 25 is a side view of a portion of a method in accordance with one embodiment of a present invention.
Figure 26:
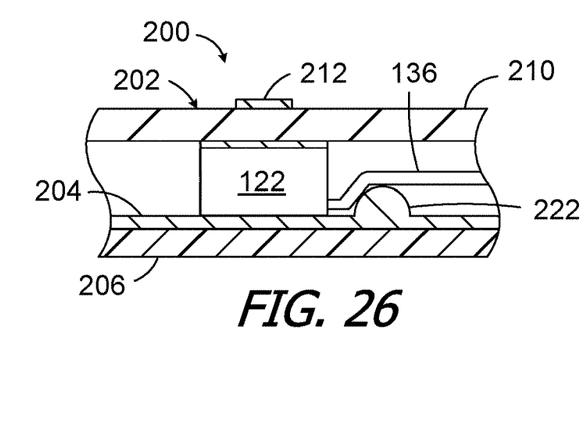
FIG. 26 is a partial section view of a portion of a method in accordance with one embodiment of a present invention.
Figure 27:
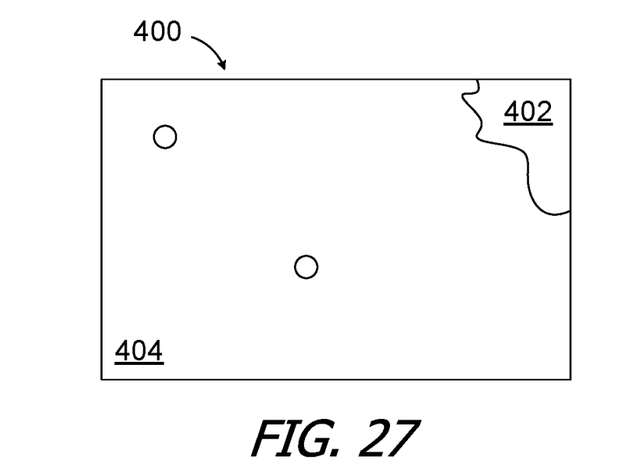
FIG. 27 is a top cutaway view of a mold in accordance with one embodiment of a present invention.

The exemplary method includes placing a contact workpiece 302 onto fixture 300 at the basal end marker 310b, and placing a lead wire 136 within the workpiece (FIGS. 17 and 18). Next, as illustrated in FIG. 19, heat and pressure are applied to the contact workpiece 302 to form the contact 122. The heat and pressure may be applied to the workpiece 302 with a weld tip 312, such as a molybdenum weld tip, in a resistance welding process. The steps illustrated in FIGS. 17-19 may then be repeated to form the remainder of the contacts 122. Referring to FIGS. 20 and 21, the lead wires 136 connected to the remaining contacts extend over the previously prepared contacts. Turning to FIG. 22, the wire carriers 208 may be formed by depositing the material from which the wire carriers are formed (e.g., LSR) onto the contacts 122 and over the lead wires 136. Any excess wire carrier material between the contacts may be removed. The rod holders 212 may then be mounted onto the wire carriers 208 (FIG. 23) and the lumen formation rod 210 may be inserted into the rod holders (FIG. 24) to complete the contact assembly 202. In other implementations, the rod holders 212 may be mounted onto the carriers 208 with the lumen formation rod 210 already in place. Turning to FIG. 25, the contact assembly 202 may then be secured to the shell 204 to complete the electrode array sub-assembly 200. As the contacts 112 reach the bottom of the channel 220, the strain relief protrusions 222 deflect the portions of the contact wires 136 adjacent to the associated contact as can be seen in FIG. 26. The malleable strip 206 may be secured to the shell 204 before the contact assembly 202 is secured to the shell (as shown) or after the contact assembly is secured to the shell.

Figure 28:
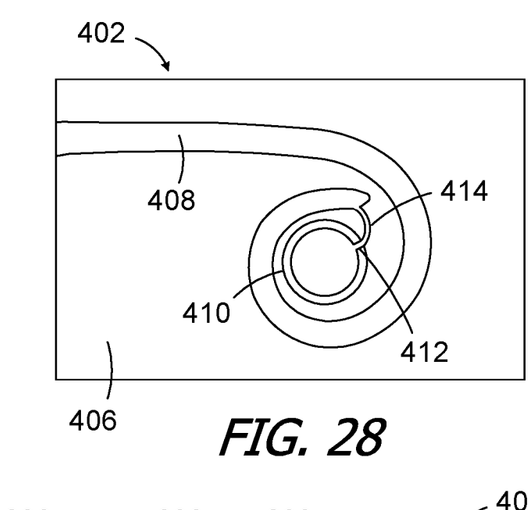
FIG. 28 is a top view of a portion of the mold illustrated in FIG. 27.
Figure 29:
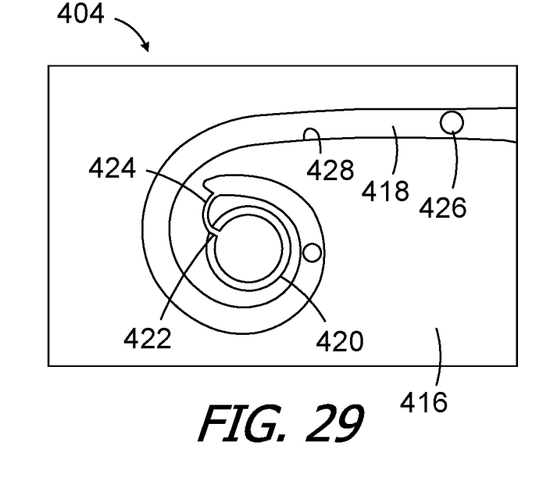
FIG. 29 is a bottom view of a portion of the mold illustrated in FIG. 27.

Turning to the molding process, and referring to FIGS. 27-30, one example of a mold into which the exemplary electrode array sub-assembly 200 may be inserted is generally represented by reference numeral 400. The exemplary mold 400 includes a first mold part 402 and a second mold part 404 that may be placed over the first mold part to complete the mold 400 in the manner illustrated in FIG. 27. A clamp, screws or other suitable instrumentality (not shown) may be used to hold the mold parts 402 and 404 together. Referring more specifically to FIG. 28, the mold part 402 includes a plate 406 with a channel 408 in the shape of a portion of the electrode array, an anchor 410 with a slot 412 for the malleable member 206, and a slot 414 that extends from the apical end of the channel 408 to the anchor slot 412. Similarly, as shown in FIG. 29, the mold part 404 includes a plate 416 with a channel 418 in the shape of a portion of the electrode array, an anchor 420 with a slot 422 for the malleable member 206, and a slot 424 that extends from the apical end of the channel 418 to the anchor slot 422. The cochlear lead wing 118 (FIG. 4) may be formed with another mold (not shown) that abuts mold 400 in the appropriate location.

Figure 30:
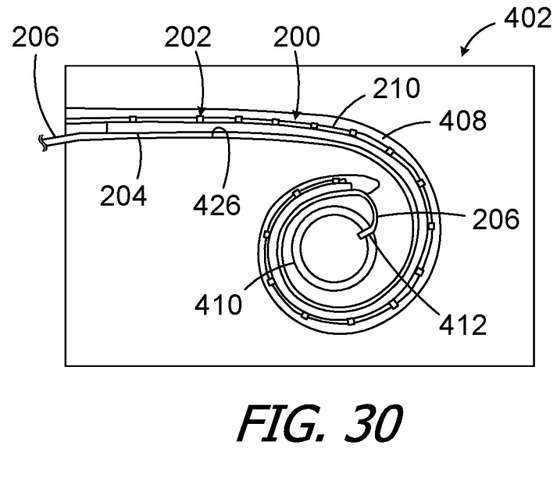
FIG. 30 is a top view of a portion of a method in accordance with one embodiment of a present invention.

The exemplary electrode array sub-assembly 200 and associated malleable member 206 may be inserted into the mold 400 by first securing the malleable member 206 to the anchor 410 of the first mold part 402. This may be accomplished by inserting the apical end of the malleable member 206 into the anchor slot 412. The malleable member 206 and attached sub-assembly 200 may then be wound around and into the channel 408. The malleable member 206 may be pressed against the surface 426 of the channel 408, as shown in FIG. 30, to properly position the sub-assembly 200 within the mold 400. The second mold part 404 may then be placed onto the first mold part 402 such that the malleable member 206 and attached electrode array sub-assembly 200 will be within the channel 418. The apical end of the malleable member 206 will enter the anchor slot 422, and the malleable member 206 will be positioned against the channel surface 428. The channels 408 and 418 will together define a mold cavity. The LSR or other suitable resilient material may then be injected (or otherwise introduced) into the mold cavity to form the flexible body 120. In those instances where the introduced resilient material is the same material that is used to form the shell 204, wire carriers 208 and rod holders 212, the resilient material combines to form a one piece, unitary structure formed from a single common material. After the resilient material hardens, the mold parts 402 and 404 may be separated from one another. The partially completed electrode array may be removed from the mold 400 along with the attached malleable member 206 and wing 118. The malleable member 206 may be removed from the partially completed electrode array by, for example, placing the partially completed electrode array and attached malleable member 206 in an IPA bath. The lumen formation rod 210 may also be removed.

Figure 31:
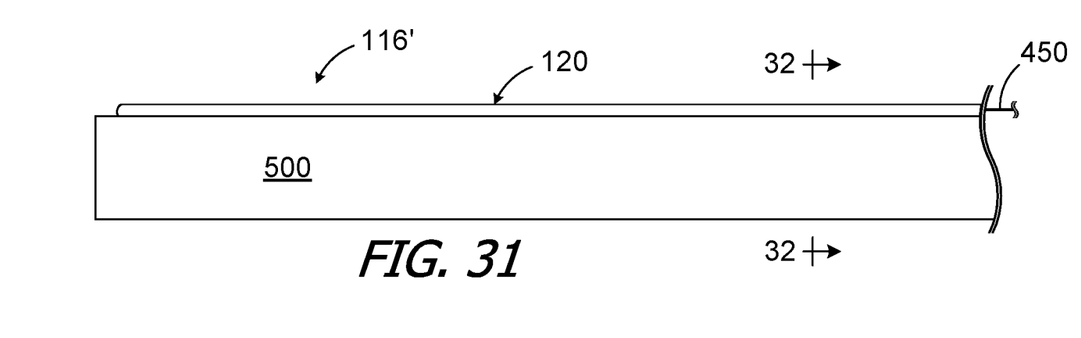
FIG. 31 is a side view of a portion of a method in accordance with one embodiment of a present invention.
Figure 32:
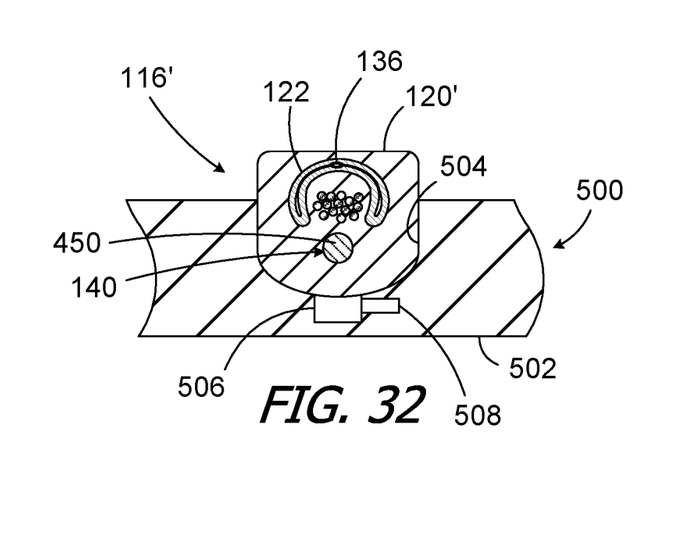
FIG. 32 is a section view taken along line 32-32 in FIG. 31.
Figure 33:
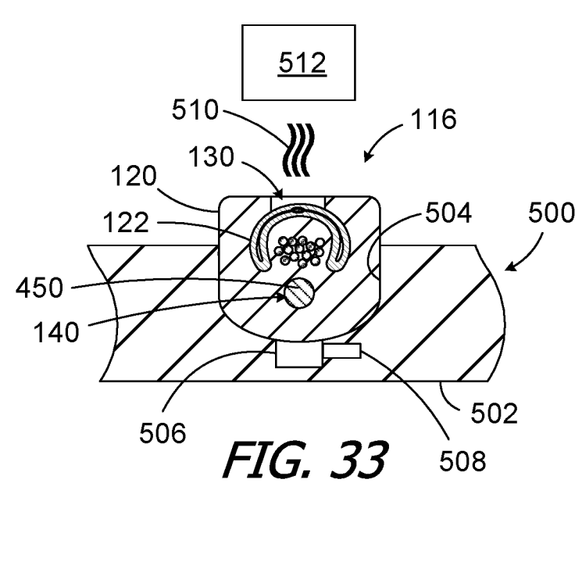
FIG. 33 is a section view of a portion of a method in accordance with one embodiment of a present invention.

In the illustrated implementation, portions of the flexible body that were previously part of the shell must be removed from the partially completed electrode array in order to expose the contacts. Any suitable process may be employed. By way of example, but not limitation, ablation energy (e.g., a laser beam) may be used to remove material from the flexible body of a partially completed electrode array. To that end, and referring to FIGS. 31-33, a stylet 450 may be inserted into the stylet lumen 140 of a partially completed electrode array 116', and the straightened partially completed electrode array 116' may be placed onto a fixture 500 that is configured to hold the partially completed flexible body 120' in a linear and untwisted state. The exemplary fixture 500 includes a plate 502 with a groove 504 and a plurality of suction apertures 506. The suction apertures 506 are connected to a source of negative pressure (not shown) by a suction line 508. The suction force holds the flexible body 120' firmly in place. Portions of the flexibly body 120' corresponding to the windows 130 for each contact 122 are then removed from the flexible with ablation energy 510 from ablation source 512, thereby exposing the portions of contacts 122, to complete the electrode array 116. Other exemplary methods of removing material from a cochlear lead blank include, but are not limited to, mechanical removal methods (e.g., surface abrasion such as rubbing or grit blasting). As noted above with reference to FIGS. 6-8, the width of the window 130 is not limited to the illustrated width.

Figure 34:
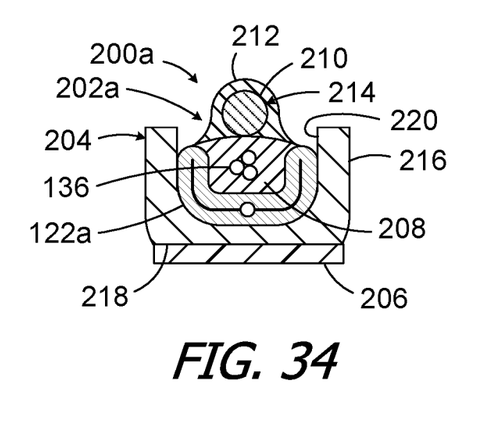
FIG. 34 is a section view of a cochlear lead electrode array sub-assembly in accordance with one embodiment of a present invention.
Figure 35:
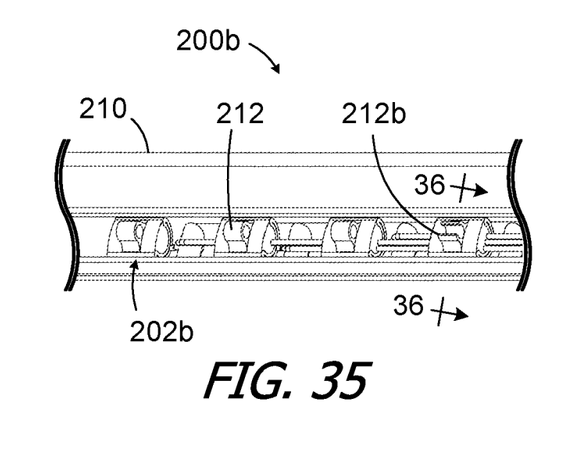
FIG. 35 is an exploded view of a cochlear lead electrode array sub-assembly in accordance with one embodiment of a present invention.
Figure 36:
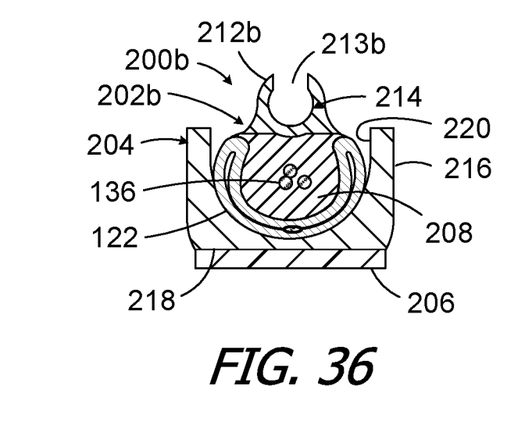
FIG. 36 is a section view taken along line 36-36 in FIG. 35.

Although the inventions disclosed herein have been described in terms of the preferred embodiments above, numerous modifications and/or additions to the above-described preferred embodiments would be readily apparent to one skilled in the art. By way of example, but not limitation, the exemplary electrode array sub-assembly 200a illustrated in FIG. 34 is essentially identical to the sub-assembly 200 and similar elements are represented by similar reference numerals. Here, however, the sub-assembly 200a includes an electrode assembly 202a with U-shaped contacts 122a. Turning to FIGS. 35 and 36, the exemplary electrode array sub-assembly 200b is essentially identical to the sub-assembly 200 and similar elements are represented by similar reference numerals. Here, however, the sub-assembly 200b includes an electrode assembly 202b with two types of rod holders, i.e., the above-described rod holders 212 as well as rod holders 212b with slots 213b. The slots 213b permit passage of the lumen formation rod 210 into the apertures 214. The rod holders 212 are associated with the apical portion of the electrode assembly 202b, while the remaining rod holders are the rod holders 212b. The inventions also include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A method, comprising the steps of:
positioning a contact assembly, including a plurality of electrically conductive contacts that are respectively connected to a plurality of lead wires, on a shell formed from a first resilient material to form an electrode array sub-assembly that includes the contacts, the lead wires, and the shell;
after the electrode array sub-assembly has been formed, positioning the electrode array subassembly in a cochlear implant electrode array mold; and
introducing a second resilient material into the mold to form a cochlear implant electrode array flexible body, on which the contacts are located, that is defined by the first and second resilient materials.

2. The method as claimed in claim 1, wherein the first and second resilient materials are the same material.

3. The method as claimed in claim 1, wherein the first and second resilient materials are not the same material.

4. The method as claimed in claim 1, wherein the contact assembly includes a plurality of wire carriers respectively located on the plurality of electrically conductive contacts.

5. The method as claimed in claim 4, wherein the contact assembly includes a plurality of rod holders respectively located on the plurality of wire carriers.

6. The method as claimed in claim 5, wherein the contact assembly includes a removable rod held by the rod holders.

7. The method as claimed in claim 6, further comprising the steps of:
removing the cochlear implant electrode array flexible body from the mold; and
removing the rod from the cochlear implant electrode array flexible body after removal from the mold.

8. The method as claimed in claim 1, wherein the shell includes an elongate channel.

9. A method, comprising the steps of:
positioning a contact assembly, including a plurality of electrically conductive contacts that are respectively connected to a plurality of lead wires, on a shell that includes an elongate channel and a plurality of strain relief protrusions within the elongate channel, and that is formed from a first resilient material, to form an electrode array sub-assembly;
positioning the electrode array subassembly in a cochlear implant electrode array mold; and
introducing a second resilient material into the mold to form a cochlear implant electrode array flexible body, on which the contacts are located, that is defined by the first and second resilient materials.

10. The method as claimed in claim 9, wherein a portion of at least some of the lead wires are deflected by the strain relief protrusions.

11. The method as claimed in claim 1, wherein the shell defines first and second longitudinal ends; and the shell is attached to a malleable strip having first and second portions and first and second longitudinal ends, at least the first longitudinal end of the malleable strip extending beyond the first longitudinal end of the shell.

12. The method as claimed in claim 11, wherein the second longitudinal end of the malleable strip extends beyond the second longitudinal end of the shell.

13. A method, comprising the steps of:
positioning a contact assembly, including a plurality of electrically conductive contacts that are respectively connected to a plurality of lead wires, on a shell formed from a first resilient material to form an electrode array sub-assembly, wherein the shell defines first and second longitudinal ends and is attached to a malleable strip having first and second portions and first and second longitudinal ends, and at least the first longitudinal end of the malleable strip extends beyond the first longitudinal end of the shell;
positioning the electrode array subassembly in a cochlear implant electrode array mold that defines a mold cavity with a curved shape;
securing the first portion of the malleable strip to the mold and bending the malleable strip into the curved shape; and
introducing a second resilient material into the mold to form a cochlear implant electrode array flexible body, on which the contacts are located, that is defined by the first and second resilient materials.

14. A method, comprising the steps of:
positioning a contact assembly, including a plurality of electrically conductive contacts that are respectively connected to a plurality of lead wires, on a shell formed from a first resilient material to form an electrode array sub-assembly, wherein the shell defines first and second longitudinal ends and is attached to a malleable strip having first and second portions and first and second longitudinal ends, and at least the first longitudinal end of the malleable strip extends beyond the first longitudinal end of the shell;
positioning the electrode array subassembly in a cochlear implant electrode array mold;
introducing a second resilient material into the mold to form a cochlear implant electrode array flexible body, on which the contacts are located, that is defined by the first and second resilient materials;
removing the cochlear implant electrode array flexible body from the mold; and
separating the malleable strip from the cochlear implant electrode array flexible body after removal from the mold.

15. The method as claimed in claim 14, further comprising the step of:
removing portions of the flexible body to expose the contacts after separating the malleable strip.

16. The method as claimed in claim 1, further comprising the step of:
removing the cochlear implant electrode array flexible body from the mold.

17. A cochlear implant electrode array made by the process of claim 1.

* * * * *